(12) United States Patent
Gupta et al.

(10) Patent No.: US 10,034,882 B2
(45) Date of Patent: Jul. 31, 2018

(54) TOFACITINIB ORALLY DISINTEGRATING TABLETS

(71) Applicant: Unichem Laboratories Limited, Mumbai (IN)

(72) Inventors: Saurabh Gupta, Uttar Pradesh (IN); Saiesh P. Phaldesai, Goa (IN); Nsk. Senthil Kumar, Chennai (IN); Milind Vinayak Sathe, Maharashtra (IN)

(73) Assignee: Unichem Laboratories Limited, Mumbai (IN)

( * ) Notice: Subject to any disclaimer, the term of this patent is extended or adjusted under 35 U.S.C. 154(b) by 0 days.

(21) Appl. No.: 15/521,496

(22) PCT Filed: Jun. 24, 2016

(86) PCT No.: PCT/IB2016/053768
§ 371 (c)(1),
(2) Date: Apr. 24, 2017

(87) PCT Pub. No.: WO2017/017542
PCT Pub. Date: Feb. 2, 2017

(65) Prior Publication Data
US 2017/0304307 A1 Oct. 26, 2017

(30) Foreign Application Priority Data
Jul. 27, 2015 (IN) .......................... 2842/MUM/2015

(51) Int. Cl.
*A61K 31/519* (2006.01)
*A61K 9/20* (2006.01)
*A61K 9/00* (2006.01)

(52) U.S. Cl.
CPC .......... *A61K 31/519* (2013.01); *A61K 9/0056* (2013.01); *A61K 9/2018* (2013.01); *A61K 9/2054* (2013.01)

(58) Field of Classification Search
CPC ..................................................... A61K 31/519
USPC ....................................................... 514/258.1
See application file for complete search history.

(56) References Cited

U.S. PATENT DOCUMENTS 7,301,023 B2 * 11/2007 Flanagan ............. C07D 487/04
544/280
2011/0257159 A1 10/2011 Cifter et al.

FOREIGN PATENT DOCUMENTS

WO WO 2015/051738 4/2015

* cited by examiner

*Primary Examiner* — Taofiq A Solola
(74) *Attorney, Agent, or Firm* — Cesari & McKenna, LLP

(57) ABSTRACT

The present invention relates to Orally Disintegrating Tablets (ODT) of Tofacitinib and its pharmaceutically acceptable salts and the process to produce the ODT. The invention further relates to ODTs comprising Tofacitinib and its pharmaceutically acceptable salts, at least one sweetening agent, at least one disintegrant and optionally other excipients. The weight of the Orally Disintegrating tablets is 200 mg or less. The invention further relates to Orally Disintegrating Tablets of Tofacitinib Citrate.

16 Claims, No Drawings

TOFACITINIB ORALLY DISINTEGRATING TABLETS

CROSS REFERENCE TO RELATED APPLICATIONS

This application is the National Stage of International Application No. PCT/IB2016/053768, filed on Jun. 24, 2016, which claims the benefit of Indian Application No. 2842/MUM/2015, filed on Jul. 27, 2015. The contents of both applications are hereby incorporated by reference in their entirety.

TECHNICAL FIELD

The present invention relates to Orally Disintegrating Tablets (ODT) of Tofacitinib and its pharmaceutically acceptable salts.

BACKGROUND OF THE INVENTION

Tofacitinib citrate chemically known as 3-{(3R,4R)-4-methyl-3-[methyl(7H-pyrrolo[2,3-d]pyrimidin-4-yl)amino]piperidin-1-yl}-3-oxo-propanenitrile, 2-hydroxypropane-1,2,3-tricarboxylate described below in figure 1 and as disclosed in the WO 02/096909 and U.S. Pat. No. 7,301,023, was approved in November 2012 by US FDA with the trade name as Xeljanz, a film coated tablet, for rheumatoid arthritis. Other indications are described in US2004/0053947. Tofacitinib and its corresponding citrate salt are useful as inhibitors of protein kinases such as the enzyme Janus Kinase 3 also referred as JAK 3. Tofacitinib Citrate is extremely bitter in taste.

FIGURE I

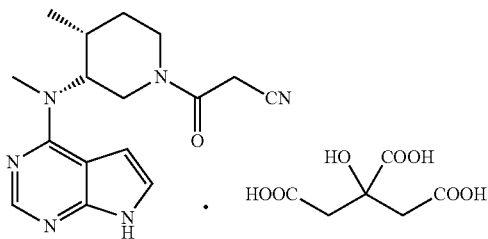

Rheumatoid Arthritis (RA) is one of the common forms of autoimmune disease. RA is a chronic systemic disease affecting the joints, muscle, tendons, connective tissues and fibrous tissue. Pain, swelling, and redness are common joint indications. RA affects over 21 million people worldwide. RA can start at any age, but the peak age of onset is between 30 and 55 years. Twice as many women are generally affected by RA than men, and the disease also impacts on the average life expectancy, shortening it by three to seven years. After 10 years, less than 50% of patients with RA can work or function normally on a day-to-day basis.

IP.com article titled "Tasocitinib Oral Tablet Composition" numbered IPCOM000202830D, dated 4 Jan. 2011, disclosed Tasocitinib immediate release oral tablets. The tablet compositions disclosed in the said article are Tofacitinib oral film coated tablet compositions with dry granulation manufacturing process. US 2012/0195933A1, describes Tasocitinib i.e. Tofacitinib composition and process to prepare the same, but is silent about ODT compositions.

USRE41783 which is basic molecule patent of Tofacitinib describes that pharmaceutical compositions may take the form of, tablets or capsules prepared by conventional means. It then describes compositions comprising binding agents etc. It does not provide any specific motivation to produce tablets without binding agents.

U.S. Pat. No. 6,956,041 and U.S. Pat. No. 7,265,221 disclose in generalized language the invention i.e. Tofacitinib may be formulated in a conventional manner using one or more pharmaceutically acceptable carriers without providing any motivation to produce orally dispersible tablet composition. These are silent about taste of Tofacitinib. Tofacitinib is extremely bitter in taste.

Possibly its extreme bitter taste has resulted into film coated compositions.

Prior art is silent about orally dispersible tablet composition or the process to prepare it.

U.S. Pat. No. 7,301,023 reports one of the polymorphic forms of Tofacitinib. Possibility of active ingredient exhibiting polymorphs creates stability issues in the composition acceptability. Their stability is unpredictable. Heating during granulation and moisture contact during wet granulation or compaction process many times lead to changes in physicochemical properties of active ingredient. Changes in molecular structures and molecular arrangements result into polymorphic change. These changes impact the performance of the formulation negatively. Stability of active or its polymorphic form is of critical importance. It is necessary for the formulation to retain the form that was incorporated.

Tofacitinib compositions as available in the prior art when tried for preparation of ODT, ODT cannot be prepared. Several processing problems were experienced. Tablets produced did not conform to the criteria of orally dispersible tablets. It was also observed that Tofacitinib when tried to formulate into tablet, leads to sticking problems. Such problems were also experienced when conventional means were tried to prepare the tablets.

Conventional formulations have several disadvantages and inability to promote the patient compliance is one of the main disadvantages. Conventional compositions are not patient friendly. Disadvantage of conventional formulation is that it has to be swallowed with water. Difficulties in taking pills or tablets with water are known. As a result, aged persons, children and the people on the move often experience difficulty in complying. RA patients are normally found in the age group above 35. As age increases, the gravity tends to increase. In older age population, patient compliance is a known problem. Conventional compositions further deteriorate the compliance. Existing composition of Tofacitinib are not fit to be consumed as orally dispersible or chewable compositions as Tofacitinib is extremely bitter.

Albeit Tofacitinib is bitter in taste, there is a need to provide a patient friendly composition of Tofacitinib. There is a need for Tofacitinib composition which can be taken without the rigors and hardships of swallowing it with water.

Tofacitinib crumbles and disintegrates and these undesirable properties make it difficult to formulate into dispersible tablet.

The bitter taste of Tofacitinib poses a great challenge for the development of orally disintegrating tablets (ODTs) formulation. Besides bitter taste, developing ODT is not simple.

Not every active pharmaceutical ingredient can be formulated into ODT. There are several limitations, like, stability of active, its processability, its ability to go into solution from tablet, its ability to support a defect free tablet formation and of all ability to combine with sweetener to mask the unpleasant or bitter taste and yet produce a stable orally disintegrating composition. Sometimes although sweeteners are added, there is unpleasant bitter after taste. These are just some of the limitations. Similarly there may be several other limitations which are active ingredient specific and can't be guessed or foreseen. Therefore, formulating an ODT is a challenge. Normally if the tablet weight is reduced several processing problems are faced for example, poor blend flow, tablet picking, sticking and all other compressibility issues. Therefore producing orally disintegrating tablets with reduced weight is a further challenge.

Orally disintegrating tablets (ODTs) have gained considerable attention as a preferred alternative to conventional tablets and capsules due to better patient compliance especially for the pediatric, geriatric, psychiatric patients and patients with nausea, vomiting and motion sickness complications. ODTs are solid dosage forms containing medicinal substances which disintegrate rapidly, usually within a matter of seconds, when placed upon the tongue. Orally disintegrating tablets are appreciated by a significant segment of populations particularly who have difficulty in swallowing. ODTs with good taste and flavor increase the acceptability of bitter drugs by various groups of population.

Orally disintegrating tablets (ODTs) disintegrate or dissolve in the mouth rapidly. Resulting liquid in the mouth can be swallowed easily. No additional water is required to be administered. This special property of ODT provides the convenience of a tablet formulation, ease of handling yet provides the ease of swallowing provided by a liquid formulation. Besides ease of administration ODTs give pleasant mouth feel. ODTs encourage patients to adhere to medication, especially the elderly patients and children who have difficulty in swallowing conventional tablets. ODTs ensure accurate dosing better than oral liquids. Ease of swallowing the tablet that is liquefied in the mouth is of immense importance when water is not available to swallow the tablet as well as in specific conditions or when the patient is not in a condition to use water and swallow the conventional tablet.

Hence, there is a need of a patient's friendly Tofacitinib Citrate ODT formulation. There is a need of a process to produce a Tofacitinib Citrate ODT formulation avoiding drawbacks of processes used to produce conventional tablets. Present invention discloses some such processes and ODT compositions. Invention also describes direct compression manufacturing process. Secondly, there is a pressing need to have a Tofacitinib composition which is in the form of smaller tablet yet orally dispersible. ODT of the present invention rapidly disintegrates in the buccal cavity, dispersing the contents and has a pleasant taste with smooth creamy mouthfeel. It can be taken without water, so it ensures better patient compliance.

OBJECT OF THE INVENTION

The object of the present invention is to provide orally disintegrating tablets of Tofacitinib or its pharmaceutically acceptable salts, more particularly Tofacitinib Citrate salt.

Another object of the present invention is to provide Tofacitinib Citrate ODT for better patient compliance.

Yet another object of the invention is to produce taste masked orally dispersible tablet of Tofacitinib or its pharmaceutically acceptable salts.

Yet another objective of the present invention is to provide Tofacitinib ODT with reduced weight.

Yet another objective of the present invention is to provide simple and cost effective process for preparing ODT compositions of Tofacitinib or its pharmaceutically acceptable salts.

SUMMARY OF THE INVENTION

Present invention provides Tofacitinib Citrate ODT. Present invention provides Tofacitinib Citrate ODT for better patient compliance. Present invention provides simple, cost effective and efficient process for preparing ODT compositions of Tofacitinib Citrate.

Present invention teaches ODT, specific compositions of Tofacitinib and its pharmaceutically acceptable salts with sweetening agents such as Sucralose and Aspartame and a disintegrant.

Present invention also teaches the process to produce ODT compositions with weight of 200 mg or less than 200 mg.

Tofacitinib Citrate is mixed with at least one sweetening agent and at least one disintegrant optionally with other excipients to produce pre-lubricated blend with satisfactory content uniformity. Blending time depends upon the type of blender used and volume of contents in the blender. Lubricant is mixed with the pre-lubricated blend to ensure adequate lubrication. This lubricated blend is subjected to compression to produce orally dispersible tablet.

Tofacitinib Citrate is mixed with at least one sweetening agent and at least one disintegrant, optionally with other excipients to produce pre-lubricated blend with satisfactory content uniformity. Blending time depends upon the type of blender used and volume of contents in the blender. Lubricant is mixed with the pre-lubricated blend to ensure adequate lubrication. This lubricated blend is subjected to compression to produce orally dispersible tablet having weight less than 200 mg.

DETAILED DESCRIPTION OF THE INVENTION

Present invention provides Tofacitinib Citrate ODT. Present invention provides Tofacitinib Citrate ODT for better patient compliance. Present invention provides simple, cost effective and efficient process for preparing ODT compositions of Tofacitinib Citrate. Present invention also teaches the process to produce ODT compositions with weight of 200 mg or less than 200 mg.

Tofacitinib Citrate is mixed with at least one sweetening agent and at least one disintegrant optionally with other excipients and is subjected to compression to produce orally dispersible tablet.

Tofacitinib Citrate is mixed with at least one sweetening agent and at least one disintegrant optionally with other excipients and is subjected to compression to produce orally dispersible tablet having tablet weight less than 200 mg.

Invention resides in combining Tofacitinib with sweetening agent and at least one disintegrant optionally with other excipients and is subjected to compression to produce orally dispersible tablet.

The process to produce ODT of Tofacitinib or its pharmaceutically acceptable salts in may be described as follows:

1. Tofacitinib Citrate, Diluent, Disintegrant, Sweetener and flavor were blended in suitable blender. Contents were blended to produce pre-lubricated blend to ensure content uniformity.

2. To the pre-lubricated blend was added lubricant and mixed to produce lubricated blend.
3. Lubricated blend was compressed suitable compression machine to form tablets.

The process to produce ODT of Tofacitinib or its pharmaceutically acceptable salt, more particularly citrate salt comprises following steps:
1. Tofacitinib Citrate, Mannitol, Microcrystalline Cellulose, Crospovidone, Sucralose and flavor were blended in a double cone blender of 1 liter capacity. Contents were blended for 20 minutes to produce pre-lubricated blend. Approximately 50% volume of the blender was occupied.
2. To the pre-lubricated blend was added magnesium stearate and mixing was done for 3 minutes to produce lubricated blend.
3. Lubricated blend was compressed on Rimek 8 station single rotary compression machine to form tablets.

In another preferred embodiment Tofacitinib Citrate ODT is prepared as follows:
1. Tofacitinib Citrate, Mannitol, Microcrystalline Cellulose, Croscarmellose sodium, Sucralose and flavor were blended in a double cone blender of 1 liter capacity. Contents were blended for 20 minutes to produce pre-lubricated blend. Approximately 50% volume of the blender was occupied.
2. To the pre-lubricated blend was added magnesium stearate and mixing was done for 3 minutes to produce lubricated blend.
3. Lubricated blend was compressed on Rimek 8 station single rotary compression machine to form tablets.

In another preferred embodiment Tofacitinib Citrate ODT is prepared as follows:
1. Tofacitinib Citrate, Microcelac 100, Croscarmellose sodium, Sucralose and flavor were blended in a double cone blender of 1 liter capacity. Contents were blended for to produce pre-lubricated blend. Approximately 50% volume of the blender was occupied.
2. To the pre-lubricated blend was added magnesium stearate and mixing was done for 3 minutes to produce lubricated blend.
3. Lubricated blend was compressed on Rimek 8 station single rotary compression machine to form tablets.

As mentioned in forgoing text, actives pose problems while formulating into a tablet if tablet weight is reduced. Surprisingly in compositions of the present invention wherein Tofacitinib Citrate is an active ingredient, it was observed that tablet weight can be reduced substantially i.e. by 25% and yet it was possible to formulate an ODT conveniently. One can further reduce the quantity of filler or diluent to achieve further reduced weight tablets.

Tofacitinib Citrate ODT with tablet weight less than 200 mg is produced as follows:
1. Tofacitinib Citrate, Mannitol, Microcrystalline Cellulose, Croscarmellose sodium, Sucralose and flavor were blended in a double cone blender. Contents were blended for 20 minutes to produce pre-lubricated blend. Approximately 50% volume of the blender was occupied. Content uniformity was satisfactory.
2. To the pre-lubricated blend was added magnesium stearate and mixing was done for 3 minutes to produce lubricated blend.
3. Lubricated blend was compressed on Rimek 8 station single rotary compression machine to form tablets.

In another preferred embodiment, Tofacitinib Citrate ODT with tablet weight less than 200 mg is prepared as follows
1. Tofacitinib Citrate, Mannitol, Microcrystalline Cellulose, Crospovidone, Sucralose and flavor were blended in a double cone blender. Blending was done for the period at least 20 minutes to produce pre-lubricated blend. Approximately 50% volume of the blender was occupied. Content uniformity was satisfactory.
2. To the pre-lubricated blend was added magnesium stearate and mixing was done for 3 minutes to produce lubricated blend.
3. Lubricated blend was compressed on Rimek 8 station single rotary compression machine to form tablets.

Tofacitinib Citrate ODT with tablet weight less than 200 mg is produced as follows:
1. Tofacitinib Citrate, Microcelac 100, Croscarmellose sodium, Sucralose and flavor were blended in a double cone blender. Contents were blended for 20 minutes to produce pre-lubricated blend. Approximately 50% volume of the blender was occupied. Content uniformity was satisfactory.
2. To the pre-lubricated blend was added magnesium stearate and mixing was done for 3 minutes to produce lubricated blend.
3. Lubricated blend was compressed on Rimek 8 station single rotary compression machine to form tablets.

In another preferred embodiment, Tofacitinib Citrate ODT with tablet weight less than 200 mg is prepared as follows:
1. Tofacitinib Citrate, Microcelac 100, Crospovidone, Sucralose and flavor were blended in a double cone blender. Blending was done for the period at least 20 minutes to produce pre-lubricated blend. Approximately 50% volume of the blender was occupied. Content uniformity was satisfactory.
2. To the pre-lubricated blend was added magnesium stearate and mixing was done for 3 minutes to produce lubricated blend.
3. Lubricated blend was compressed on Rimek 8 station single rotary compression machine to form tablets.

Tofacitinib and Tofacitinib citrate are used interchangeably. Orally disintegrating tablets and orally dispersible tablets mean the same. Compositions of the present invention can be prepared using conventional techniques of common tableting methods known in the art such as direct compression, wet granulation, dry granulation and extrusion/melt granulation. Direct compression is simple, cost effective and efficient and the most convenient method to carry out the invention. Compositions of the present invention when in tablet form may be shaped such as oval, hexagonal, triangle, parallelogram, almond, peanut, round, pentagonal, and trapezoidal. The preferred shapes are round, oval.

Compositions of the present invention with weight ranging from 80 mg to 1600 mg can be formulated satisfactorily. As mentioned earlier, it is possible to formulate tablet compositions with still lower weights. Compositions with weight less than 80 mg can be formulated after doing modulations of fillers, disintegrating agents or other excipients.

Compositions of the present invention include tablets and compacted or compressed powder compositions obtained by compressing or otherwise forming the compositions to form a solid having a defined shape. With Tofacitinib or its pharmaceutically acceptable salts, sweetening agent and disintegrant, other excipients that may be used are diluents or fillers or bulking agents, colorants, flavors, souring agents, stabilizers, viscosity builders, salivating agents, surfactants, glidents, solubilizers lubricants and flavors.

Many times particle size distribution of active plays important role in formulating a tablet that conforms to regulatory norms and in producing desired effect in body. It also impacts content uniformity. Tofacitinib Citrate with particle size distribution (PSD) of D90 not more than 50 μm gives better results. However Tofacitinib Citrate with PSD of D90 above 50 μm may also be used. As the particle size increases, the process needs to be modified accordingly. The modification mechanisms would include milling or modulating quantity of glidant or flow improver or modulating quantity of disintegrants or addition of solubilizers or use of suitable granulation such as wet granulation or dry granulation of the contents. High solubility of Tofacitinib and its pharmaceutically acceptable salts allows use of bigger particle size. Therefore, Tofacitinib Citrate with PSD of D90 more than 50 μm can be used for formulating ODT.

Suitable diluents used according to present invention are selected from mannitol, lactose, microcrystalline cellulose, dextrose, sucrose, sorbitol, starch and the like or mixtures or co-processed mixtures like Microcelac 100 or the mixtures thereof in the range of about 50 to 95% w/w. Carbohydrates i.e. monosaccharide, disaccharide, oligosaccharide or polysaccharide are useful diluents to be used. Examples of carbohydrates include, but are not limited to, monosaccharides such as glucose, fructose, maltose or xylitol, disaccharides such as trehalose, glucose, galactose or and oligosaccharides and polysaccharides such as dextrates and maltodextrins. Optionally, co-processed or composite excipients may also be incorporated into the compositions of the invention. Co-processed or composite excipient comprises of at least one water soluble excipient and water insoluble inorganic excipient such as calcium silicate may be used. The water soluble excipient can be a carbohydrate selected from monosaccharide, disaccharide, oligosaccharide or polysaccharide. Examples of carbohydrates include, but are not limited to, monosaccharides such as sorbitol, glucose, dextrose, fructose, maltose or xylitol, disaccharides such as sucrose, trehalose, lactose, glucose, galactose or mannitol, and oligosaccharides and polysaccharides such as dextrates and maltodextrins. Preferably, the water soluble excipient is mannitol. Commercial available mixtures of water insoluble and water soluble excipients may also be used. These mixtures may also be prepared manually in the lab or on manufacturing floor.

The compositions of the invention also include at least one disintegrant. The term disintegrant also includes superdisintegrant. The disintegrants used in the composition includes but not limited to, natural, modified or pre-gelatinized starch, carboxymethylcellulose, starch, crospovidone, croscarmellose sodium, sodium starch glycolate, low-substituted hydroxypropyl cellulose and the like or mixtures thereof in the range of about 0.1 to 20% w/w. Effervescent disintegrating systems can also be employed. A disintegrant may be employed singularly or more than one disintegrants may also be employed. Higher concentrations of disintegrants may as well be employed.

Suitable sweeteners used according to present invention are selected from sucralose, aspartame, saccharin sodium and the like or mixtures thereof. Although concentrations lower than 0.1% w/w may be used, the sweetening agent when present in the concentration of 0.1 to 5% w/w, gives better results.

Suitable flavoring agents used according to present invention are selected from mint, orange, lemon, peppermint, vanilla, bubble gum, strawberry, cherry, caramel, raspberry, tutti-fruity, banana and the like or mixtures thereof. Flavoring agent is present in the concentration of 0.1-1.0% w/w and is satisfactory. Although flavoring agent in lesser concentrations than 0.1% w/w or in higher concentrations than 1% w/w can be used, use of flavoring agent concentration in the vicinity of 0.4% w/w gives better composition. The concentration of flavoring agent is flavor specific and may be modulated depending upon the flavour/s used.

Suitable glidants used according to present invention are selected from colloidal silicon dioxide, silica gel, precipitated silica, talc and the like or mixtures thereof in the range of about 0 to 10% w/w.

Examples of the suitable lubricant used according to present invention include, but are not limited to magnesium stearate, stearic acid, sodium stearyl fumarate, calcium stearate, talc, glyceryl behenate and the like or mixtures thereof in the range of about 0.1 to 5% w/w.

Compositions of the present invention may also optionally include salivating agents such as, but not limited to, sodium chloride, micronized polyethylene glycol or precipitated micronized silica. Salivating agents improve the disintegration properties of the compositions.

Examples of solubilizers which may be optionally included in the compositions of the present invention include, but are not limited to, cetostearyl alcohol, lecithin, cholesterol, medium-chain glyceride, diethanolamine, ethyl oleate, ethylene glycol palmitostearate, glycerin, glyceryl monostearate, polyoxyethylene castor oil glycoside, isopropyl myristate, monoethanolamine, oleic acid, propylene glycol, polyoxyethylene alkyl ether, polyethylene sorbitan fatty acid ester, polyoxyethylene stearate, propylene glycol alginate, sorbitan fatty acid ester, stearic acid, sunflower oil, triethanolmine, and mixtures thereof. These are optional.

Stabilizers which may be optionally included in the compositions of the present invention may also include, but not limited to citric acid, benzoic acid, sodium benzoate, and the like.

Surfactants help in quick wetting of the tablet in mouth. Examples of surfactants that can be used optionally in the present invention include, but are not limited to, glyceryl monooleate, polyethylene alkyl ether, sodium lauryl sulfate, polyoxyethylene sorbitan fatty acid ester, sodium docusate, sorbic acid, sorbitan fatty acid ester, and mixtures thereof.

Sour taste is liked by few. As souring agents improve the taste. Accordingly, optionally souring agents that can be included in the compositions of the present invention include, but are not limited to, citric acid, Tartaric acid, monosodium fumarate and the like.

Viscolizers increase the viscosity of the solution resulting from the liquification of the tablet caused due to saliva. Optionally viscosity building agents that may be included in the compositions of the present invention include such as, but not limited to, polyalkylene oxides; polyols; starch and starch-based polymers; chitosan; polysaccharide gums; polyethylene oxide, hydroxypropyl cellulose, hydroxypropyl methyl cellulose, hydroxyethyl cellulose, sodium carboxymethylcellulose, calcium carboxymethylcellulose, methyl cellulose, polyacrylic acid, gum acacia, gum tragacanth, xanthan gum, guar gum and polyvinyl alcohol and copolymers and mixtures thereof.

The present invention and the foregoing description of the invention provides adequate direction for producing orally dispersible tablet of Tofacitinib and its pharmaceutically acceptable salts.

Pharmaceutically acceptable salt of Tofacitinib is acid addition salt. The acid addition salt is selected from Tofacitinib salts of citrate, acid citrate, hydroiodide, hydrobromide, hydrochloride, sulfate, nitrate, bisulfate, phosphate, acetate, acid phosphate, lactate, tartrate, bitartrate, succinate, maleate, fumarate, gluconate, saccharate, benzoate, ethanesulfonate, methanesulfonate, p-toluenesulfonate benzenesulfonate, and pamoate salts.

Simple and cost effective process meaning the process that is simple to execute, involves lesser number of steps than number of steps known in producing currently available non ODT formulations. Because the process of present invention involves lesser number of steps, it is cost effective.

EXAMPLES

The present invention describes the Tofacitinib Citrate ODT formulations with the following details:

Example 1

| Component | Quantity/Tablet (mg) |
|---|---|
| Tofacitinib Citrate | 8.078* |
| Mannitol (Pearlitol 200 SD) | 123.122 |
| Microcrystalline Cellulose (Avicel PH 112) | 50.000 |
| Croscarmellose sodium (Ac di Sol) | 10.000 |
| Sucralose | 3.000 |
| Mint/Orange Flavor | 0.800 |
| Magnesium stearate | 5.000 |
| Tablet Core Total | 200.000 |

*8.078 mg of Tofacitinib Citrate is equivalent to 5.0 mg Tofacitinib. The amount of Tofacitinib may be adjusted based on assay and moisture content with Microcrystalline Cellulose accordingly.

Manufacturing Process:
1. Tofacitinib Citrate, Mannitol, Microcrystalline Cellulose, Croscarmellose sodium, Sucralose and flavor were blended in a double cone blender of 1 liter capacity. Contents were blended for 20 minutes to produce pre-lubricated blend. Approximately 50% volume of the blender was occupied.
2. To the pre-lubricated blend was added magnesium stearate and mixing was done for 3 minutes to produce lubricated blend.
3. Lubricated blend was compressed on Rimek 8 station single rotary compression machine to form tablets.

Example 2

| Component | Quantity/Tablet (mg) |
|---|---|
| Tofacitinib Citrate | 8.078* |
| Mannitol (Pearlitol 200 SD) | 123.122 |
| Microcrystalline Cellulose (Avicel PH 112) | 50.000 |
| Crospovidone (Polyplasdone XL-10) | 10.000 |
| Sucralose | 3.000 |
| Mint/Orange Flavor | 0.800 |
| Magnesium stearate | 5.000 |
| Tablet Core Total | 200.000 |

*8.078 mg of Tofacitinib Citrate is equivalent to 5.0 mg Tofacitinib. The amount of Tofacitinib may be adjusted based on assay and moisture content with Microcrystalline Cellulose accordingly Manufacturing Process:
1. Tofacitinib Citrate, Mannitol, Microcrystalline Cellulose, Crospovidone, Sucralose and flavor were blended in a double cone blender of 1 liter capacity. Contents were blended for 20 minutes to produce pre-lubricated blend. Approximately 50% volume of the blender was occupied.
2. To the pre-lubricated blend was added magnesium stearate and mixing was done for 3 minutes to produce lubricated blend.
3. Lubricated blend was compressed on Rimek 8 station single rotary compression machine to form tablets.

Example 3

| Component | Quantity/Tablet (mg) |
|---|---|
| Tofacitinib Citrate | 8.078* |
| Mannitol (Pearlitol 200 SD) | 84.322 |
| Microcrystalline Cellulose (Avicel PH 112) | 37.500 |
| Croscarmellose sodium (Ac di Sol) | 12.000 |
| Sucralose | 3.000 |
| Mint/Orange Flavor | 0.600 |
| Magnesium stearate | 4.500 |
| Tablet Core Total | 150.000 |

*8.078 mg of Tofacitinib Citrate is equivalent to 5.0 mg Tofacitinib. The amount of Tofacitinib may be adjusted based on assay and moisture content with Microcrystalline Cellulose accordingly.

Manufacturing Process:
1. Tofacitinib Citrate, Mannitol, Microcrystalline Cellulose, Croscarmellose sodium, Sucralose and flavor were blended in a double cone blender. Contents were blended for 20 minutes to produce pre-lubricated blend. Approximately 50% volume of the blender was occupied. Content uniformity was satisfactory.
2. To the pre-lubricated blend was added magnesium stearate and mixing was done for 3 minutes to produce lubricated blend.
3. Lubricated blend was compressed on Rimek 8 station single rotary compression machine to form tablets.

Example 4

| Component | Quantity/Tablet (mg) |
|---|---|
| Tofacitinib Citrate | 8.078* |
| Mannitol (Pearlitol 200 SD) | 84.322 |
| Microcrystalline Cellulose (Avicel PH 112) | 37.500 |
| Crospovidone (Polyplasdone XL-10) | 12.000 |
| Sucralose | 3.000 |
| Mint/Orange Flavor | 0.600 |
| Magnesium stearate | 4.500 |
| Tablet Core Total | 150.000 |

*8.078 mg of Tofacitinib Citrate is equivalent to 5.0 mg Tofacitinib. The amount of Tofacitinib may be adjusted based on assay and moisture content with Microcrystalline Cellulose accordingly.

Manufacturing Process:
1. Tofacitinib Citrate, Mannitol, Microcrystalline Cellulose, Crospovidone, Sucralose and flavor were blended in a double cone blender. Contents were blended for 20 minutes to produce pre-lubricated blend. Approximately 50% volume of the blender was occupied. Content uniformity was satisfactory.
2. To the pre-lubricated blend was added magnesium stearate and mixing was done for 3 minutes to produce lubricated blend.
3. Lubricated blend was compressed on Rimek 8 station single rotary compression machine to form tablets.

Example 5

| Component | Quantity/Tablet (mg) |
|---|---|
| Tofacitinib Citrate | 8.078* |
| Microcelac 100 | 121.822 |
| Croscarmellose sodium (Ac di Sol) | 12.000 |
| Sucralose | 3.000 |
| Mint/Orange Flavor | 0.600 |
| Magnesium stearate | 4.500 |
| Tablet Core Total | 150.000 |

*8.078 mg of Tofacitinib Citrate is equivalent to 5.0 mg Tofacitinib. The amount of Tofacitinib may be adjusted based on assay and moisture content with Microcrystalline Cellulose accordingly.

Manufacturing Process:
1. Tofacitinib Citrate, Microcelac 100, Croscarmellose sodium, Sucralose and flavor were blended in a double cone blender. Contents were blended for 20 minutes to produce pre-lubricated blend. Approximately 50% volume of the blender was occupied. Content uniformity was satisfactory.
2. To the pre-lubricated blend was added magnesium stearate and mixing was done for 3 minutes to produce lubricated blend.
3. Lubricated blend was compressed on Rimek 8 station single rotary compression machine to form tablets.

Example 6

| Component | Quantity/Tablet (mg) |
|---|---|
| Tofacitinib Citrate | 8.078* |
| Microcelac 100 | 121.822 |
| Crospovidone (Polyplasdone XL-10) | 12.000 |
| Sucralose | 3.000 |
| Mint/Orange Flavor | 0.600 |
| Magnesium stearate | 4.500 |
| Tablet Core Total | 150.000 |

*8.078 mg of Tofacitinib Citrate is equivalent to 5.0 mg Tofacitinib. The amount of Tofacitinib may be adjusted based on assay and moisture content with Microcrystalline Cellulose accordingly.

Manufacturing Process:
1. Tofacitinib Citrate, Microcelac 100, Croscarmellose sodium, Sucralose and flavor were blended in a double cone blender. Contents were blended for 20 minutes to produce pre-lubricated blend. Approximately 50% volume of the blender was occupied. Content uniformity was satisfactory.
2. To the pre-lubricated blend was added magnesium stearate and mixing was done for 3 minutes to produce lubricated blend.
3. Lubricated blend was compressed on Rimek 8 station single rotary compression machine to form tablets.

Example 7

Tablets produced from above example number 1 to 6 were tasted and were free from bitter taste.

Example 8

Tablets produced in examples 1-6 were packed in HDPE bottle and in Alu-Alu pack. These packs were studied for 3 months at 40° C. at 75% RH. There wasn't any significant change wrt description, Average weight, Dissolution in 30 minutes, impurities, Assay, Disintegration time and Hardness of the tablets. Tablets disintegrated in less than 30 seconds.

We claim:

1. An orally disintegrating tablet comprising tofacitinib or its pharmaceutically acceptable salt, at least one sweetening agent, and at least one disintegrant,
   wherein the at least one sweetening agent is present at 0.1-5 wt % and the at least one disintegrant is present at 0.1-20 wt %.

2. The orally disintegrating tablet as claimed in claim 1, wherein the pharmaceutically acceptable salt of tofacitinib is tofacitinib citrate.

3. The orally disintegrating tablet as claimed in claim 1 having weight of 200 mg or less.

4. A process to produce an orally disintegrating tablet containing tofacitinib or its pharmaceutically acceptable salt comprising steps of:
   a. blending tofacitinib or its pharmaceutically acceptable salt, a disintegrant, a sweetener, and optionally, a diluent and a flavoring agent in a suitable blender for a period of 20 minutes to produce a pre-lubricated blend;
   b. optionally mixing a lubricant with the pre-lubricated blend obtained in step a for a period of 3 minutes to produce a lubricated blend; and
   c. compressing the pre-lubricated blend obtained in step a or the lubricated blend obtained in step b on a rotary compression machine to form the orally disintegrating tablet.

5. The process as claimed in claim 4, wherein the pharmaceutically acceptable salt of tofacitinib is tofacitinib citrate.

6. An orally disintegrating tablet comprising tofacitinib citrate, mannitol, microcrystalline cellulose, crospovidone, sucralose and a flavoring agent.

7. A process to produce an orally disintegrating tablet comprising tofacitinib or its pharmaceutically acceptable salt, comprising steps of:
   a. blending tofacitinib citrate, mannitol, microcrystalline cellulose, crospovidone, sucralose and a flavoring agent in a suitable blender for a period of 20 minutes to produce a pre-lubricated blend;
   b. mixing magnesium stearate with the pre-lubricated blend obtained in step a for a period of 3 minutes to produce a lubricated blend; and
   c. compressing the lubricated blend obtained in step b on a rotary compression machine to form the orally disintegrating tablet.

8. The orally disintegrating tablet as claimed in claim 1, wherein the at least one disintegrant is selected from the group consisting of natural, modified or pre-gelatinized starch, carboxymethylcellulose, starch, crospovidone, croscarmellose sodium, sodium starch glycolate, low-substituted hydroxypropyl cellulose, and a mixture thereof.

9. The orally disintegrating tablet as claimed in claim 1, wherein the at least one sweetening agent is selected from the group consisting of sucralose, aspartame, saccharin sodium and a mixture thereof.

10. The orally disintegrating tablet as claimed in claim 1, further comprising at least one diluent, at least one lubricant, and at least one flavoring agent.

11. The orally disintegrating tablet as claimed in claim 10, wherein the at least one diluent is selected from the group consisting of mannitol, lactose, microcrystalline cellulose, dextrose, sucrose, sorbitol, starch, Microcelac 100, and a mixture thereof.

12. The orally disintegrating tablet as claimed in claim 10, wherein the at least one diluent is present at 50-95 wt %.

13. The orally disintegrating tablet as claimed in claim 10, wherein the at least one lubricant is selected from the group consisting of magnesium stearate, stearic acid, sodium stearyl fumarate, calcium stearate, talc, glyceryl behenate, and a mixture thereof.

14. The orally disintegrating tablet as claimed in claim 10, wherein the at least one lubricant is present at 0.1-5 wt %.

15. The orally disintegrating tablet as claimed in claim 10, wherein the at least one flavoring agent is selected from the group consisting of mint flavor, orange flavor, lemon flavor, peppermint flavor, vanilla flavor, bubble gum flavor, strawberry flavor, cherry flavor, caramel flavor, raspberry flavor, tutti-fruity flavor, banana flavor, and a mixture thereof.

16. The orally disintegrating tablet as claimed in claim 10, wherein the at least one flavoring agent is present at 0.1-1.0 wt %.

\* \* \* \* \*